(12) United States Patent
Holdsworth

(10) Patent No.: US 10,281,644 B2
(45) Date of Patent: May 7, 2019

(54) METHOD AND APPARATUS FOR CALIBRATING LOW-LIGHT LEVEL OPTICAL IMAGING SYSTEMS

(71) Applicant: David Wayne Holdsworth, London (CA)

(72) Inventor: David Wayne Holdsworth, London (CA)

( * ) Notice: Subject to any disclaimer, the term of this patent is extended or adjusted under 35 U.S.C. 154(b) by 8 days.

(21) Appl. No.: 15/893,502

(22) Filed: Feb. 9, 2018

(65) Prior Publication Data

US 2018/0224592 A1     Aug. 9, 2018

Related U.S. Application Data

(60) Provisional application No. 62/456,841, filed on Feb. 9, 2017.

(51) Int. Cl.

| | |
|---|---|
| *F21V 8/00* | (2006.01) |
| *G06T 7/90* | (2017.01) |
| *G06T 3/40* | (2006.01) |
| *G01N 21/76* | (2006.01) |
| *G01N 21/64* | (2006.01) |

(Continued)

(52) U.S. Cl.
CPC ......... *G02B 6/0083* (2013.01); *G01N 21/278* (2013.01); *G01N 21/6486* (2013.01); *G06T 3/40* (2013.01); *G06T 7/001* (2013.01); *G06T 7/90* (2017.01); *G01N 21/6456* (2013.01); *G01N 21/763* (2013.01); *G02F 1/1368* (2013.01); *G02F 2201/52* (2013.01);

(Continued)

(58) Field of Classification Search
None
See application file for complete search history.

(56) References Cited

U.S. PATENT DOCUMENTS

| | | | | |
|---|---|---|---|---|
| 7,969,428 B2 * | 6/2011 | Miller | ................ | G09G 3/2003 345/204 |
| 2006/0221322 A1 * | 10/2006 | Tinnemans | ......... | G03F 7/70291 355/69 |

(Continued)

*Primary Examiner* — Crystal L Hammond
(74) *Attorney, Agent, or Firm* — Brunet & Co. Ltd.

(57) ABSTRACT

Laboratory optical imaging systems for fluorescence and bioluminescence use a sensitive charge-coupled device (CCD) camera to produce quantitative measurements of very low light intensity, detecting signals from specimens labeled with optical fluorophores or luminescent emitters. Commercially available systems typically provide quantitative measurements of light output, in units of radiance (photons $s^{-1}$ $cm^{-2}$ $SR^{-1}$) or intensity (photons $s^{-1}$ $cm^{-2}$). We describe a quality assurance system for low-light imagers, based on an LED-illuminated thin-film transistor (TFT) liquid crystal display module. The light intensity is controlled by pulse-width modulation of the backlight, producing intensity values ranging from $1\times10^6$ photons $s^{-1}$ $cm^{-2}$ to $4\times10^{13}$ photons $s^{-1}$ $cm^{-2}$. The lowest light intensity values are produced by very short backlight pulses (i.e. approximately 10 μs), repeated every 300 s. This light source provides a stable, traceable intensity standard that can be used for routine quality assurance of optical imaging systems.

5 Claims, 12 Drawing Sheets

(51) Int. Cl.
*G01N 21/27* (2006.01)
*G06T 7/00* (2017.01)
*G02F 1/1368* (2006.01)

(52) U.S. Cl.
CPC ............... *G06T 2207/10024* (2013.01); *G06T 2207/30121* (2013.01); *G06T 2207/30208* (2013.01)

(56) References Cited

U.S. PATENT DOCUMENTS

| | | | |
|---|---|---|---|
| 2007/0257946 A1* | 11/2007 | Miller | G09G 3/2003 345/694 |
| 2014/0119593 A1* | 5/2014 | Filler | G06T 1/0064 382/100 |
| 2018/0120553 A1* | 5/2018 | Leshem | G02B 21/365 |
| 2018/0130170 A1* | 5/2018 | Filler | G06T 7/246 |

* cited by examiner

METHOD AND APPARATUS FOR CALIBRATING LOW-LIGHT LEVEL OPTICAL IMAGING SYSTEMS

REFERENCE TO SEQUENCE LISTING, A TABLE, OR A COMPUTER PROGRAM LISTING COMPACT DISC APPENDIX

Not Applicable

BACKGROUND OF THE INVENTION

The widespread availability of bench-top optical imaging systems for use with small animals and cell cultures has resulted in the rapid growth of research involving bioluminescent and fluorescent labels (Graves 2004; Ntziachristos 2006; Klose 2009; Leblond 2010). Laboratory optical imaging systems provide rapid, routine quantitative measurements of light intensity, facilitating comparison of the uptake and expression of optical labels. While these systems often provide values in quantitative units of radiance or intensity, there is often no means for routine quality assurance (Resch-Genger 2005; Sevick-Muraca 2013). This makes it difficult to compare values between different systems, or to maintain confidence in reported values following maintenance or system upgrades. It can also be challenging to ensure that light intensity values are being reported accurately over different fields of view or acquisition parameters.

Specialized calibration and monitoring devices have been previously described (Troy 2004; Nelson 2005; Esmonde-White 2011; Vonwil 2014; Bentz 2016), but no routine solution is available for monitoring of all aspects of performance of optical imaging systems, including linearity, gain, read noise, spatial resolution, and dark noise. Ideally, such a system would be compact, inexpensive, and stable. Optical imaging systems for use with small-animals are extremely sensitive, typically capable of detecting intensity values of less than 10,000 photons $s^{-1}$ $cm^{-2}$. On the other hand, much higher light intensities would be useful during setup and preview of the calibration device, facilitating real-time operation. For these reasons, the calibration system must be capable of providing light intensity values over an extremely broad range—typically over 7 orders of magnitude.

BRIEF SUMMARY OF THE INVENTION

We describe the implementation of an LED-backlit thin-film transistor (TFT) liquid crystal display (LCD) for use as an optical imaging calibration device. The light intensity is controlled by pulse-width modulation of the LED backlight, providing several orders of magnitude of control over display radiance. The TFT LCD module can be configured to produce uniform exposure patterns in white light, or individual colour channels (i.e. red, green, or blue). The pixel matrix display can be configured to display image test patterns to characterize spatial resolution and geometric scaling. This device can provide routine quality assurance for laboratory fluorescence and bioluminescence optical imaging systems.

There are several aspects of commercially available optical imaging system that constrain the design of the optical calibration phantom. The device must be small enough to fit inside the imaging chamber, and be positioned on the tray in place of animals or specimens. There are two acquisition configurations used in current commercial optical imaging systems: viewed from the bottom (using a 45° mirror) or viewed from the top (Leblond, Davis et al. 2010). Therefore, the proposed optical calibration system should be designed to operate in either orientation. The system must be introduced into the optical chamber without compromising the light-tight seal, and be controlled externally (either by wired connection or wirelessly). The system should be capable of presenting operator-selectable images on the display, including uniform illumination (over the range $1 \times 10^6$ photons $s^{-1}$ $cm^{-2}$ to $4 \times 10^{13}$ photons $s^{-1}$ $cm^{-2}$), geometric patterns (to verify pixel spacing, spatial resolution and geometric uniformity), and coloured images to verify spectral response (such as red, green, or blue patterns).

BRIEF DESCRIPTION OF THE DRAWINGS

Embodiments will now be described more fully with reference to the accompanying drawings in which.

DETAILED DESCRIPTION OF THE INVENTION

Figure 1:
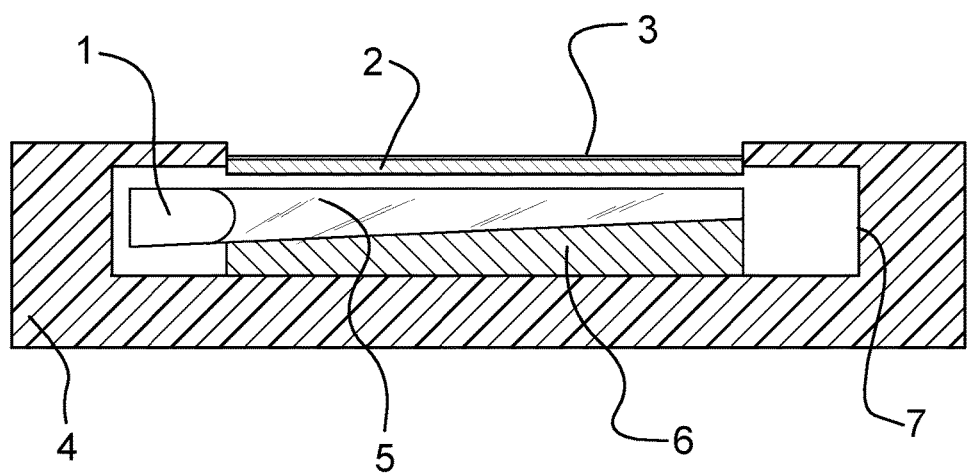
FIG. 1 is a sectional illustration of the thin-film transistor (TFT) liquid-crystal display (LCD) display.

Referring to FIG. 1, one embodiment of the calibration device is based on a 46 mm (diagonal) LCD TFT display (ST7735R) 7 with 128×160 pixel resolution and an 18-bit (262,144) colour display. The display is housed in a 1.5 cm thick opaque plastic housing 4, which allows it to be positioned face-up or inverted, depending on the imaging geometry of the system being tested. The display comprises a light-emitting diode backlight 1 that illuminates a transparent light guide 5. A reflector 6 ensures that the light propagates towards a diffuser 2 and exits the device through a thin-film transistor display matrix 3.

Figure 2:
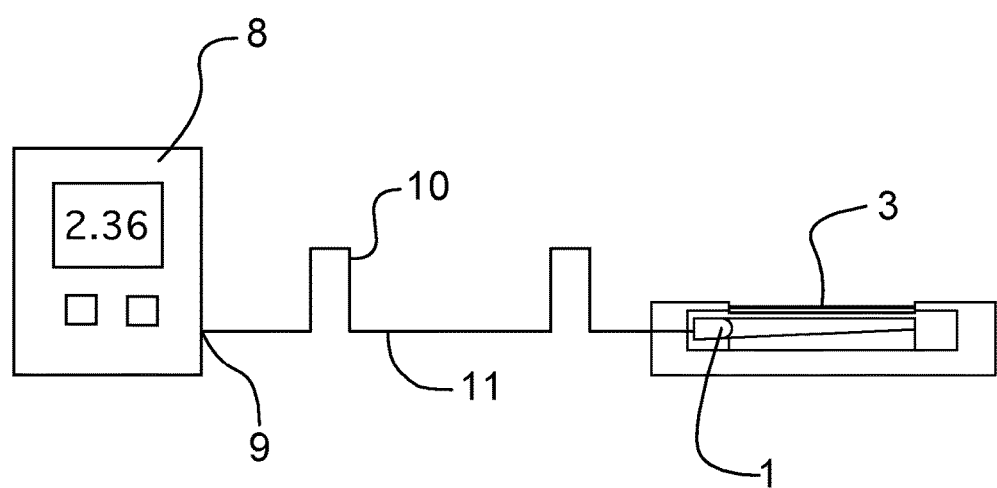
FIG. 2 illustrates modulation of the duty-cycle of the LED light source that back-illuminates the display.

Referring to FIG. 2, the display is controlled by a dedicated microcontroller system 8 (ATmega328P), which uploads image data and controls the voltage on a digital output 9. Manipulation of the duty cycle of the voltage output thus controls the average intensity of the LED backlight 1 and consequently the intensity of illumination from the LCD-TFT display 3. The controller is configured to be able to vary the temporal duration of a voltage pulse 10 (referred to as the ON interval), as well as the interval between successive pulses 11 (referred to as the OFF interval). The ON interval can be selected from between 10 μs and 10,000 μs, while the OFF interval can be selected from between 1 ms and 300,000 ms. This approach provide a very wide range of effective optical intensities during time exposures imaging of up to 5 minutes in duration.

Figure 3:
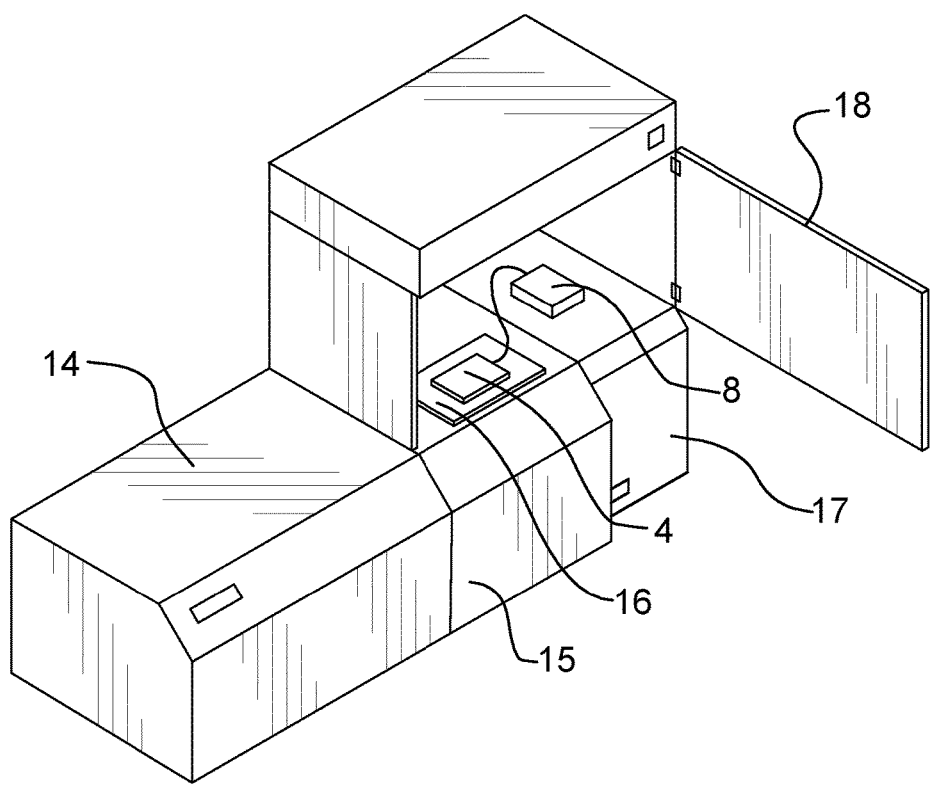
FIG. 3 illustrates the optical calibration device in operation in a typical low-light level imaging system (FX-Pro, Carestream/Bruker)

Referring to FIG. 3, the calibration device is designed to be compatible with conventional low-light level imaging systems, such as the FX-Pro (Carestream/Bruker). The FX-Pro is an inverted imaging system, with a cooled CCD camera 17 viewing an animal or specimen situated on a transparent tray 16. In this configuration, the specimen is viewed from the bottom using a 45° mirror 15 (Cool 2013). For fluorescence imaging, the specimen can be illuminated by filtered light from a high-intensity lamp 14. The detector system 17 is a monochrome interlined CCD (2048×2048 pixels; 7.4 μm pitch) cooled to −29° C. Image magnification can be modified continuously with a mechanical zoom lens, with field of view (FOV) ranging from 20 to 200 mm. The aperture can also be mechanically controlled, with aperture settings ranging from f/2.5 to f/22. The manufacturer specifies dark-current noise of less than 0.003 electrons pixel$^{-1}$ s$^{-1}$ and <7 electrons (RMS) read noise, giving a dynamic range of greater than 4 orders of magnitude. For our study, all acquisitions were carried out with no pixel binning and no emission filters were in place during imaging. Image intensity from the TFT-LCD display can be varied over a range of duty cycles, with 12.7 μs ON in all cases, and OFF times ranging from 100 to 60,000 ms. The low-light level calibration device 4 is positioned on the imaging tray 16 and controlled by a dedicated microcontroller 8. The TFT-LCD display is controlled by a USB serial line from a laptop, with the USB cable configured to pass through the light-tight seal on the FX-Pro door 18. Custom software allows the operator to select either a uniform image over a 35×28 mm area, or a prescribed intensity pattern. Light output is calibrated with a photometer (J16, Tektronix) in units of irradiance (μW cm$^{-2}$; J6502 probe) and luminance (candelas cm$^{-2}$; J6503 probe).

Further features and embodiments of the foregoing will be evident to persons of skill in the art. The inventor intends to cover all features, embodiments and sub-combinations thereof disclosed herein. The claims are to be construed as broadly as possible with reference to the specification as a whole. The invention may further be understood with reference to the following Examples.

Figure 4:
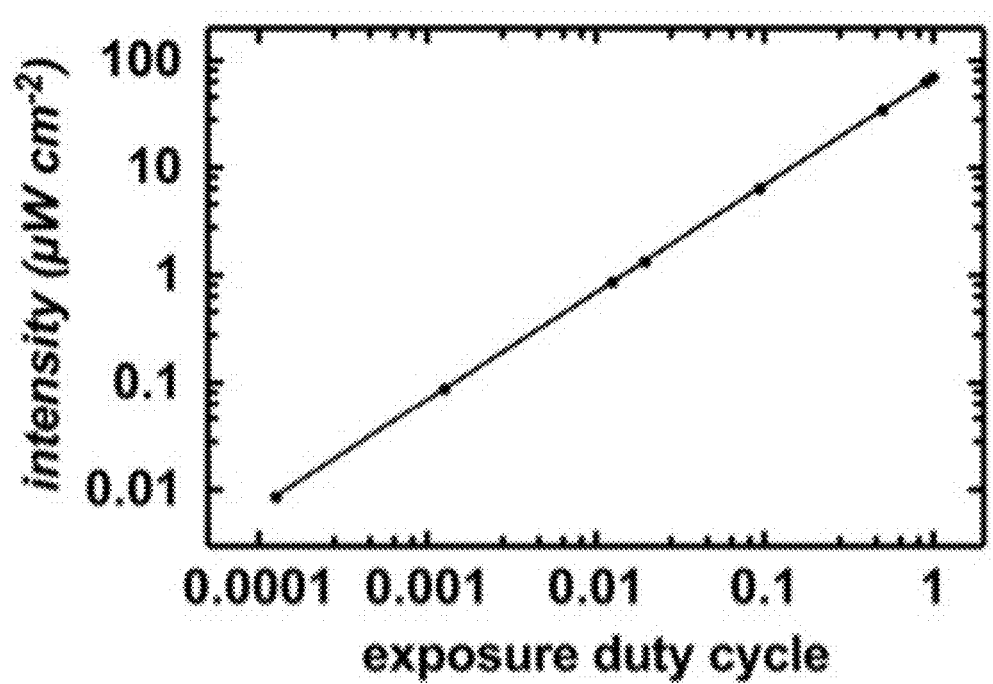
FIG. 4 illustrates calibration data, obtained using the low-intensity display and a photometer (J16/J6502, Tektronix)

Referring to FIG. 4, the intensity of the TFT-LCD display was calibrated by varying the duty cycle (over the range of 0.0001 to 1) while recording light intensity with the J6502 probe (μW cm$^{-2}$). Note that it was not possible to measure intensities lower than this with the photometer, which had reached the lower limits of sensitivity of about 0.01 μW cm$^{-2}$. FIG. 4 shows the results of this investigation; the TFT-LCD display intensity was linearly proportional to exposure duty cycle over four orders of magnitude.

Figure 5:
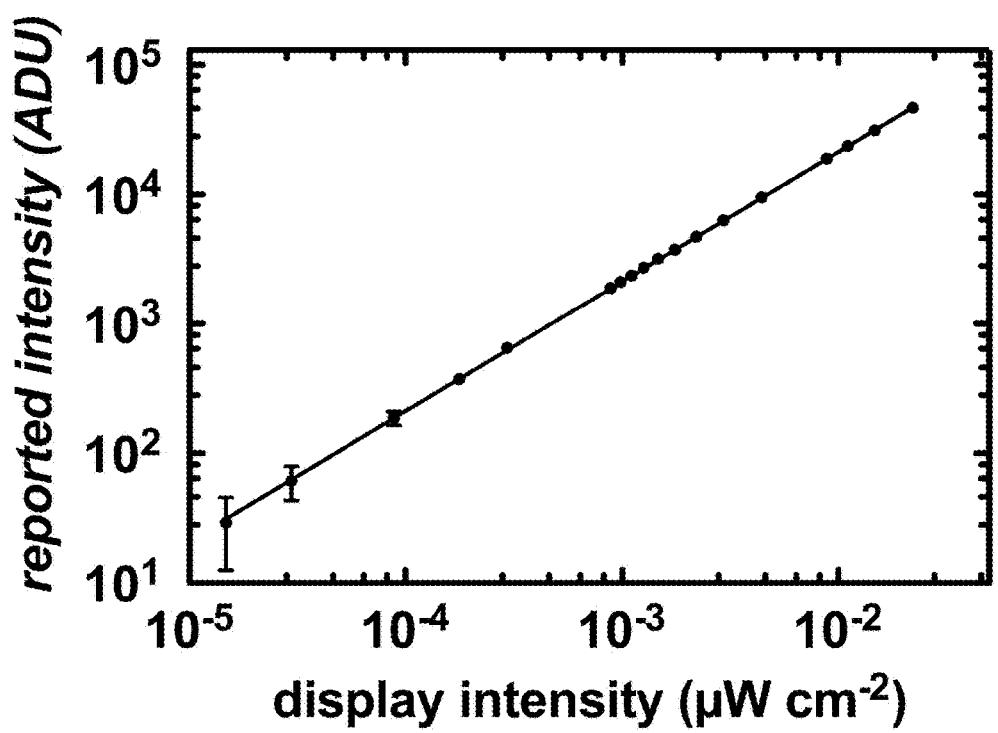
FIG. 5 illustrates the use of the low-level optical calibration device to determine the linearity of a low-light level imaging system (FX-Pro)

Referring to FIG. 5, the response of the FX-Pro imaging system was evaluated over a range of exposures, with the TFT-LCD placed inverted on the imaging tray during 1-minute acquisitions. The display intensity was varied over the range of 0.000015 μW cm$^{-2}$ to 0.022 μW cm$^{-2}$. For each acquisition, vendor-supplied software (Carestream Mich., Carestream Health Inc.) was used to determine the average intensity within a 36×28 pixel region-of-interest (ROI). FIG. 5 shows the results of this study. The reported response of the FX-Pro in arbitrary analog-to-digital units (ADUs) was linear with input exposure over four decades of intensity. The data shown in FIG. 5 can also be combined with the mean-variance analysis method to determine the absolute gain of the charge-coupled device camera (in analog-to-digital units per electron) and the read noise (in electrons) (Sperline 2005). In this case, we found the gain to be 1.994 ADU per electron, with read noise of 4.4 electrons (consistent with the manufacturer's specifications).

Figure 6:
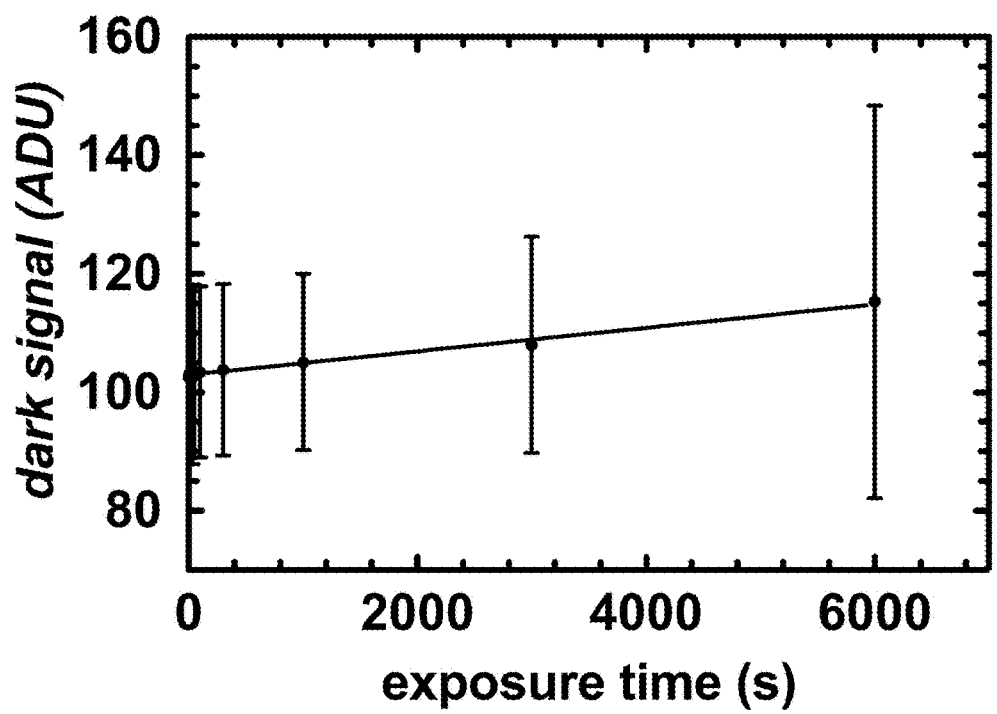
FIG. 6 illustrates the use of the low-level optical calibration device to determine the dark signal characteristics of a low-light level imaging system (FX-Pro)

Referring to FIG. 6, the calibration procedure can also include acquisitions with the LED backlight turned off, which will facilitate analysis of dark signal from the CCD detector. FIG. 6 shows the results of such an investigation, varying the exposure interval of the detector system over a range from 1 second to 6000 seconds. Dark signal obtained from this investigation was 0.003 electrons pixel$^{-1}$ s$^{-1}$, which is within the manufacturer's specifications for this device.

Figure 7:
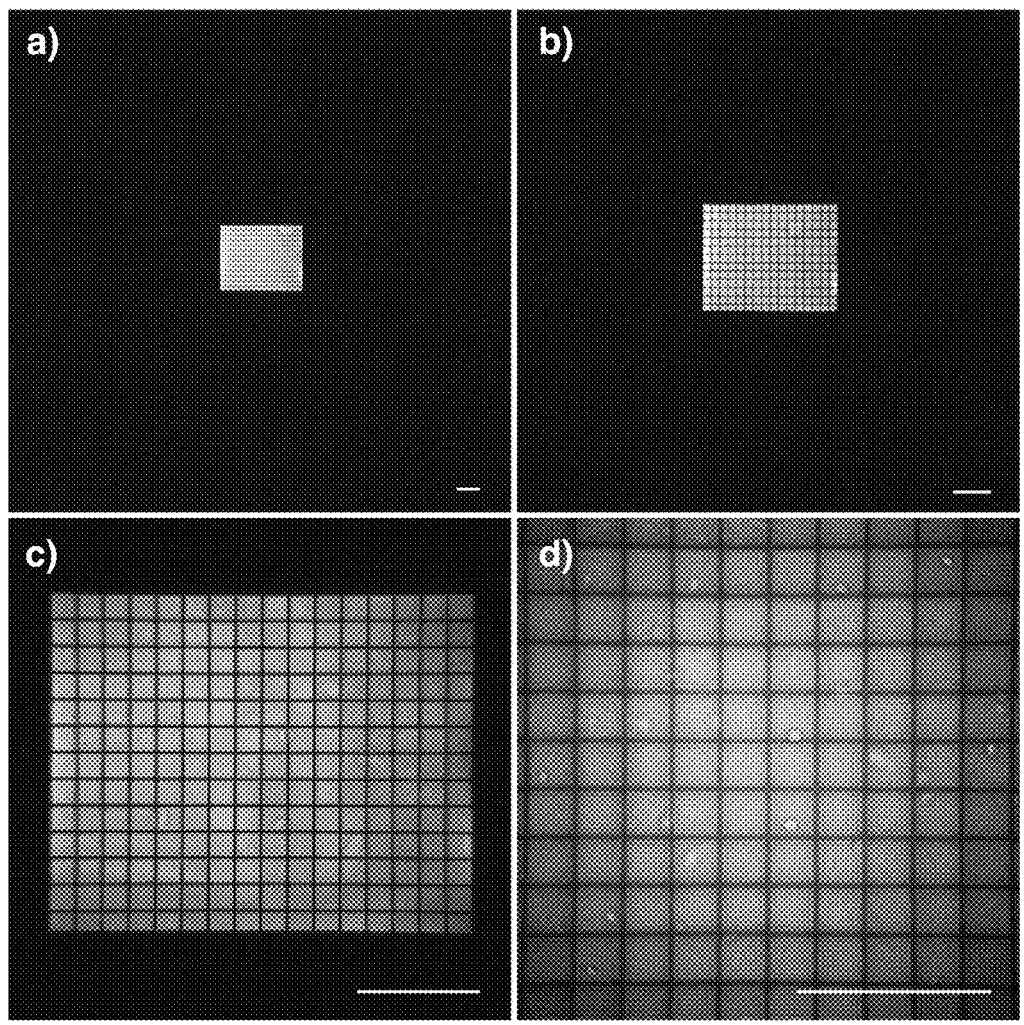
FIG. 7 illustrates the use of low-level optical calibration device to verify geometric image scale on a low-light level imaging system (FX-Pro), with field-of-view ranging from (a) 200 mm, (b) 140 mm, (c) 40 mm, and (d) 20 mm.
Figure 8:
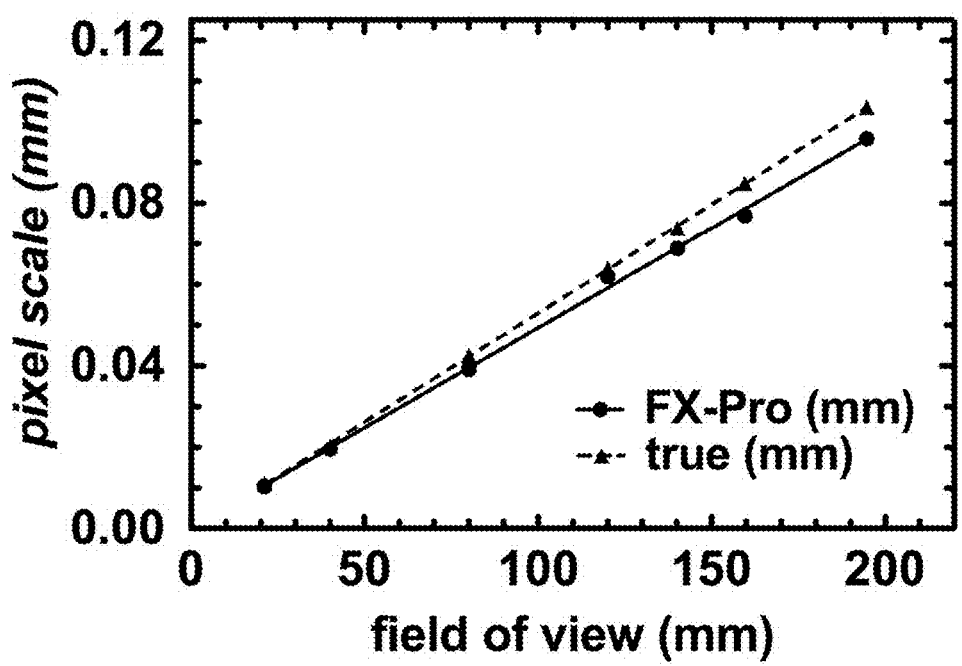
FIG. 8 illustrates the use of the low-level optical calibration device to determine geometric scaling of the low-light-level imaging system (FX-Pro) over fields-of-view ranging from 20 to 200 mm.

Referring to FIG. 7, the TFT-LCD calibration device provides the capability to assess the accuracy of geometric pixel scaling in the image. The FX-Pro, like most whole-body pre-clinical optical imaging systems, can image over an operator-selected range of magnifications. In this case, the magnification is changed by a motor-driven zoom lens, over the range of 2 to 20 cm. The image analysis software provided by the vendor (Carestream Health) determines an absolute scaling factor (i.e. pixels mm$^{-1}$) for each operator-selected FOV, facilitating quantitative measurements of area and length. For these tests, the display was configured to produce a grid pattern to assess the accuracy of geometric scaling at all FOVs. FIG. 7 illustrates the images obtained with the FX-Pro at a nominal fields-of-view ranging from 20 to 200 mm. FIG. 8 compares the true pixel scaling (as presented by the optical calibration phantom) with the reported pixel scale (as determined by the FX-Pro). We found that pixel scale was within ±6% over all FOVs.

Figure 9:
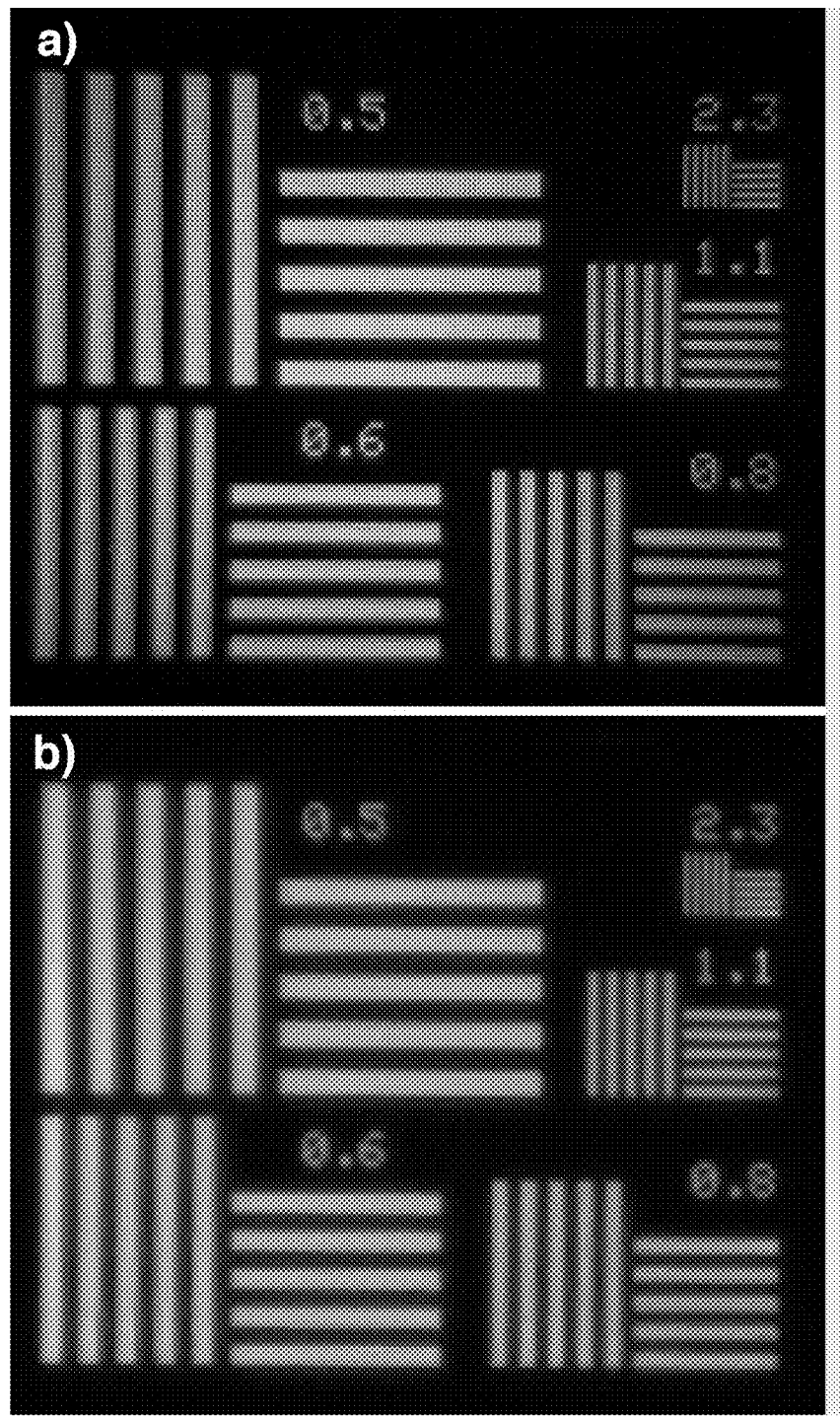
FIG. 9 illustrates the use of the low-level optical calibration device to determine spatial resolution (line-pairs per mm) of the low-light-level imaging system (FX-Pro) over fields-of-view ranging from (a) 40 to (b) 200 mm.

Referring to FIG. 9, the TFT-LCD calibration device provides the capability to assess the spatial resolution within the image. In this case the display is configured to produce intensity patterns of know spacing, ranging from 2.3 to 0.5 line-pairs mm$^{-1}$. FIG. 9 demonstrates that the FX-Pro exhibits spatial resolution exceeding 2.3 line-pairs mm$^{-1}$ over fields of view ranging from (a) 40 mm to (b) 200 mm.

Figure 10:
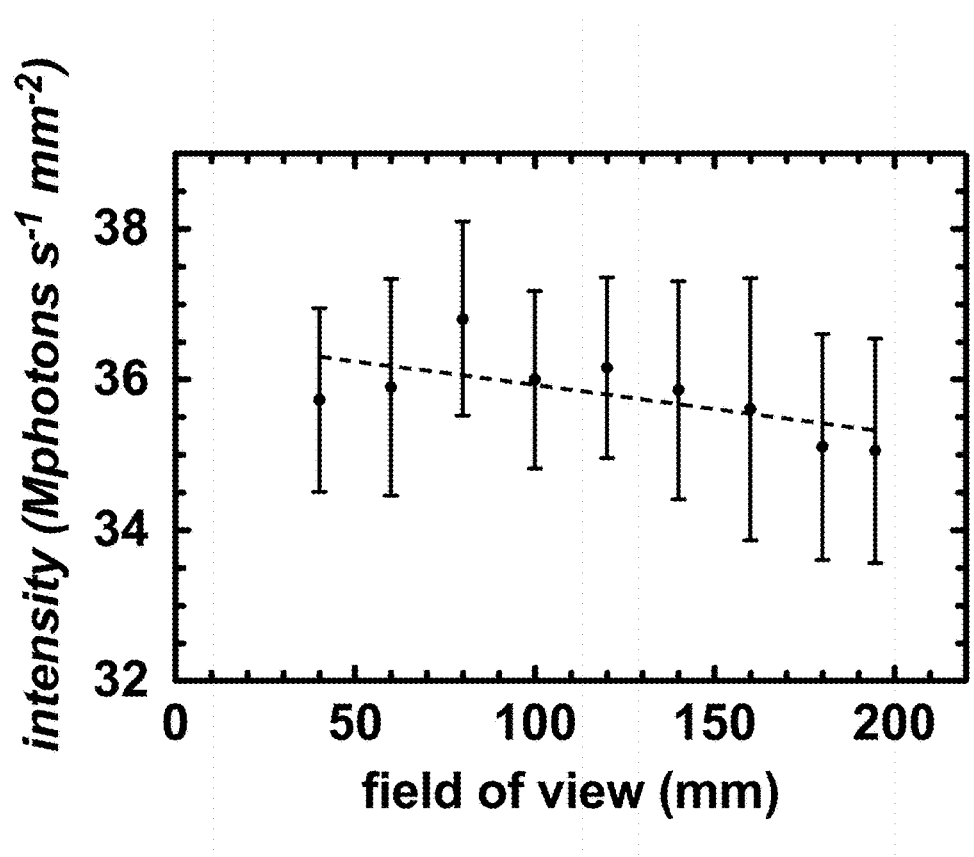
FIG. 10 illustrates the use of the low-level optical calibration device to determine reported intensity of a low-light level imaging system (FX-Pro) over fields-of-view ranging from 40 to 200 mm.

Referring to FIG. 10, the TFT-LCD calibration device provides the capability to assess the accuracy of image intensity at all image magnification settings. The image analysis software provided by the vendor (Carestream Health) is designed to account for the corresponding change in brightness, so that the reported intensity is constant at all FOVs. The TFT-LCD display provides an excellent opportunity to test this capability, by producing a constant illumination field, which can be imaged at several magnifications settings. We evaluated the reported intensity at the following FOVs: 20, 40, 80, 120, 140, and 200 mm. Average intensity was evaluated within a 36×28 pixel ROI, and was found to be constant to within ±3% over all FOVs.

Figure 11:
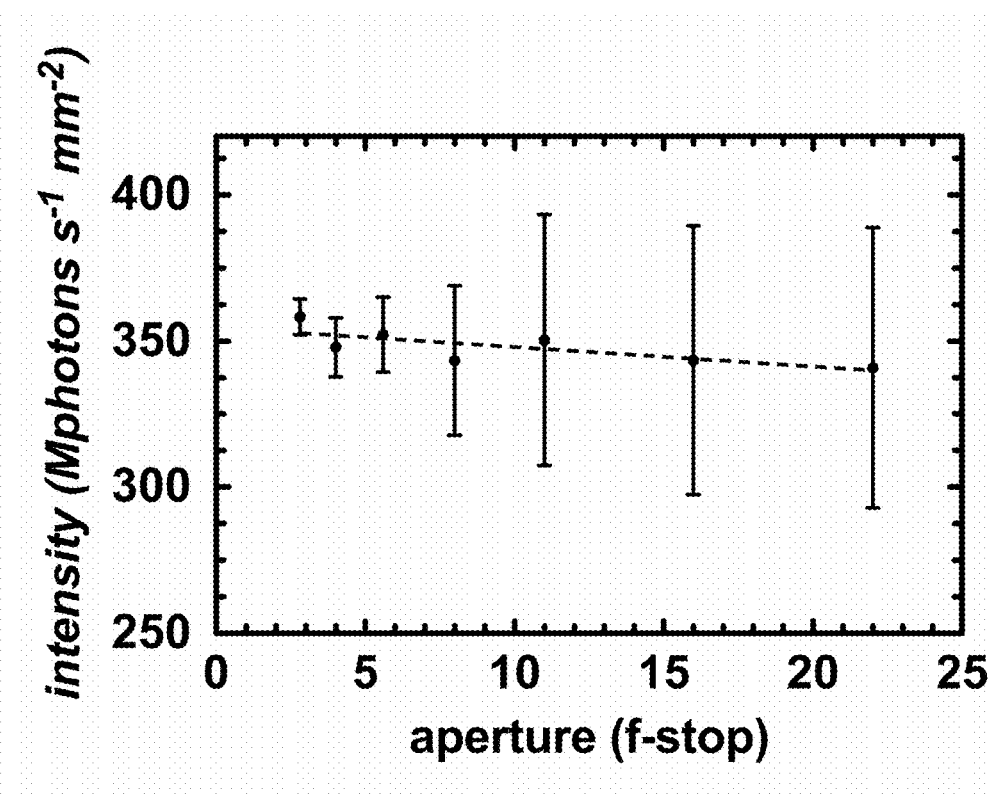
FIG. 11 illustrates the use of the low-level optical calibration device to determine reported intensity of a low-light level imaging system (FX-Pro) over aperture settings ranging from f/2.5 to f/22.

Referring to FIG. 11, the TFT-LCD calibration device provides the capability to assess the accuracy of image intensity at all lens aperture settings. The FX-Pro also has the capability to modify the lens aperture setting under computer control, allowing the operator to choose from a range of aperture settings (from f/2.5 to f/22). Again, the software is designed to record the current aperture setting, and to compensate for resulting image intensity changes as a function of lens aperture. For these tests, we used a uniform fixed-intensity pattern to assess the accuracy of brightness compensation at all f/stops. We found that reported signal intensity was within ±3% over all aperture settings.

The optical calibration phantom that we describe has the added advantage that it can be used within a regular quality assurance program to ensure that imaging systems do not drift over time. This is particularly important in a longitudinal study with live animals. We used the TFT-LCD display to evaluate image intensity at four light intensity values, and repeated these measurements after a six-month interval (during which time there was no maintenance or upgrades to system hardware or software). Image intensity values over the entire range of performance for the FX-Pro system remained constant to within ±0.7% over an 18-month interval.

Figure 12:
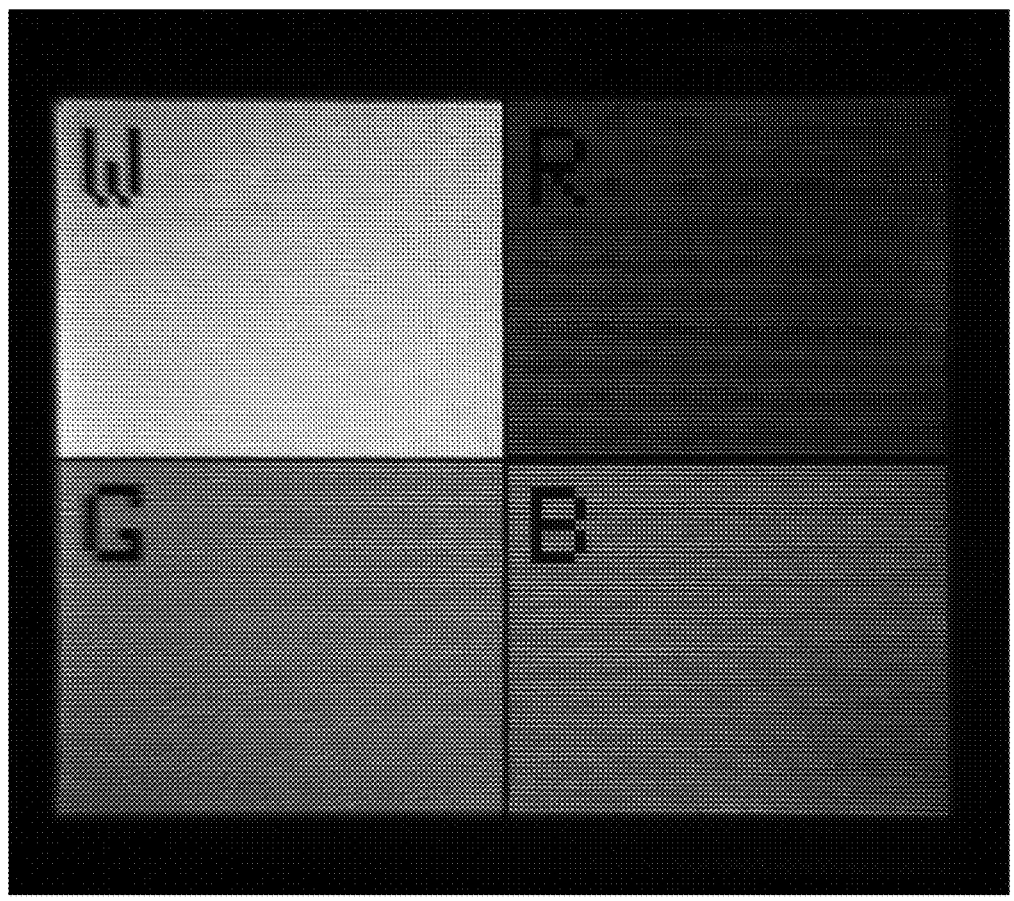
FIG. 12 illustrates the use of the low-level optical calibration device to investigate the spectral response of a low-light level imaging system (FX-Pro), providing a display of known intensity values in white (W), red (R), green (G), and blue (B) light.

Referring to FIG. 12, the TFT-LCD calibration device can also be configured to produce a colour intensity pattern, which can be used to determine the spectral response of the detector system and emission filters. FIG. 12 is the result of a monochrome acquisition with no emission filter in place, illustrating the relative intensities of white light, as well as red, green, and blue wavelengths.

REFERENCES

Bentz, B. Z., A. V. Chavan, D. Lin, E. H. Tsai and K. J. Webb (2016). "Fabrication and application of heterogeneous printed mouse phantoms for whole animal optical imaging." *Appl Opt* 55(2): 280-287.

Cool, S. K., K. Breyne, E. Meyer, S. C. De Smedt and N. N. Sanders (2013). "Comparison of in vivo optical systems for bioluminescence and fluorescence imaging." *J Fluoresc* 23(5): 909-920.

Esmonde-White, F. W., K. A. Esmonde-White, M. R. Kole, S. A. Goldstein, B. J. Roessler and M. D. Morris (2011). "Biomedical tissue phantoms with controlled geometric and optical properties for Raman spectroscopy and tomography." *Analyst* 136(21): 4437-4446.

Graves, E. E., R. Weissleder and V. Ntziachristos (2004). "Fluorescence molecular imaging of small animal tumor models." *Curr Mol Med* 4(4): 419-430.

Klose, A. D. and B. J. Beattie (2009). "Bioluminescence tomography with CT/MRI co-registration." *Conf Proc IEEE Eng Med Biol Soc* 2009: 6327-6330.

Leblond, F., S. C. Davis, P. A. Valdes and B. W. Pogue (2010). "Pre-clinical whole-body fluorescence imaging: Review of instruments, methods and applications." *J Photochem Photobiol B* 98(1): 77-94.

Nelson, M. B., B. Rice, B. R. Bates and B. V. Beeman (2005). Light calibration device for use in low level light imaging systems. U. S. Patent.

Ntziachristos, V. (2006). "Fluorescence molecular imaging." *Annu Rev Biomed Eng* 8: 1-33.

Resch-Genger, U., K. Hoffmann, W. Nietfeld, A. Engel, J. Neukammer, R. Nitschke, B. Ebert and R. Macdonald (2005). "How to improve quality assurance in fluorometry: fluorescence-inherent sources of error and suited fluorescence standards." *J Fluoresc* 15(3): 337-362.

Sevick-Muraca, E. M. and B. Zhu (2013). "The need for performance standards in clinical translation and adoption of fluorescence molecular imaging." *Med Phys* 40(4): 040402.

Sperline, R. P., A. K. Knight, C. A. Gresham, D. W. Koppenaal, G. M. Hieftje and M. B. Denton (2005). "Read-noise characterization of focal plane array detectors via mean-variance analysis." *Applied Spectroscopy* 59(11): 1315-1323.

Troy, T., D. Jekic-McMullen, L. Sambucetti and B. Rice (2004). "Quantitative comparison of the sensitivity of detection of fluorescent and bioluminescent reporters in animal models." *Mol Imaging* 3(1): 9-23.

Vonwil, D., J. Christensen, S. Fischer, O. Ronneberger and V. P. Shastri (2014). "Validation of fluorescence molecular tomography/micro-CT multimodal imaging in vivo in rats." *Mol Imaging Biol* 16(3): 350-361.

What is claimed is:

1. A method for calibrating optical intensity levels, spatial resolution and geometric scaling factors for a low-light-level imaging system, the method comprising:
   a. providing a thin-film transistor liquid crystal display module with a light-emitting diode backlight within a low-light level imaging system, to serve as a calibration phantom;
   b. modulating the average light intensity of the thin-film transistor liquid crystal display module by pulse-width modulation of the light-emitting diode backlight;
   c. calibrating the average light intensity of the thin-film transistor liquid crystal display module in absolute light intensity units;
   d. calibrating the geometric spacing of the pixels within the thin-film transistor liquid crystal display module in absolute distance units;
   e. obtaining a 2D image of the calibration phantom using a high-sensitivity, cooled charge-coupled device camera in a low-light level imaging system;
   f. determining the light intensity in the image using the low-light level imaging system;
   g. comparing the light intensity in the image with the pre-determined display intensity of the calibration phantom;
   h. deriving a fitted function that quantifies the relationship between the calibrated display intensity and the light intensity in the image reported by the low-light level imaging system;
   i. determining the spatial resolution of the system from observations of spatial frequency patterns presented on the TFT display image;
   j. determining the location of geometric control points presented on the TFT display image; and;
   k. comparing the location of the control points in the image with the pre-determined location of the control points in the phantom.

2. The method according to claim 1, wherein the modulation of light intensity of the thin-film transistor liquid crystal display module is determined by varying the temporal duration of a digital output signal, provided by a single-board micro-controller.

3. The method according to claim 2, wherein the true light intensity is determined by a photometer that is calibrated in absolute units to a National Institute for Standards and Technology (NIST) traceable source.

4. The method according to claim 3, wherein the average light intensity provided by the display can be varied over at least 8 orders of magnitude.

5. A system for calibrating optical intensity levels and geometric scaling factors for a low-light-level imaging system, comprising:
   a. a low-intensity optical calibration phantom comprising a liquid-crystal display with pulse-width modulated backlight, the phantom suitable for imaging by a low-light level bioluminescence/luminescence imaging system;
   b. a single-board micro-controller provided with machine executable instructions configured to execute a control program that varies the temporal duty cycle of the light-emitting diode backlight for the display module;
   c. the same single-board micro-controller provided with machine executable instructions configured to execute a control program that may generate geometric control points in the intensity display, with operator-selected spacing;
   d. the same single-board micro-controller provided with machine executable instructions configured to execute a control program that may generate spatial frequency patterns in the intensity display, with operator-selected spacing;
   e. a computer provided with machine executable instructions configured to execute an analysis program that determines the light intensity from an image of the phantom acquired using the low-light level imaging system, compares the reported intensity to the true intensity of the phantom, and calculates a fitted function that relates reported intensity to true intensity;
   f. a computer provided with machine executable instructions configured to execute an analysis program that determines the light intensity from an image of the phantom acquired using the low-light level imaging system, correlates the reported intensity to the calculated variance of the light intensity signal, and calculates a fitted linear function that relates mean signal to variance; and,
   g. a computer provided with machine executable instructions configured to execute an analysis program that determines the location of geometric control points in an image of the phantom acquired using the low-light level imaging system, compares the location of the control points in the image with the pre-determined location of the control points in the phantom, and calculates a correction that relates reported locations to true locations within the image.

* * * * *